(12) United States Patent
Fitzpatrick (10) Patent No.: US 8,374,679 B2
(45) Date of Patent: Feb. 12, 2013

(54) SYSTEM AND METHODS FOR DETERMINING THE ORIENTATION AND POSITION OF A BONE-IMPLANTED ANCHOR

(75) Inventor: John Michael Fitzpatrick, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 1389 days.

(21) Appl. No.: 12/035,761

(22) Filed: Feb. 22, 2008

(65) Prior Publication Data

US 2008/0234573 A1 Sep. 25, 2008

Related U.S. Application Data

(60) Provisional application No. 60/902,735, filed on Feb. 22, 2007.

(51) Int. Cl.
*A61B 5/00* (2006.01)
(52) U.S. Cl. ....................................................... 600/424
(58) Field of Classification Search .................. None
See application file for complete search history.

(56) References Cited

U.S. PATENT DOCUMENTS

| | | | | |
|---|---|---|---|---|
| 5,458,125 A | * | 10/1995 | Schweikard | 600/407 |
| 5,752,962 A | * | 5/1998 | D'Urso | 606/130 |
| 6,327,491 B1 | * | 12/2001 | Franklin et al. | 600/429 |
| 6,459,927 B1 | * | 10/2002 | Franklin et al. | 600/429 |
| 7,702,380 B1 | * | 4/2010 | Dean | 600/426 |
| 2002/0141626 A1 | | 10/2002 | Caspi | |
| 2003/0120143 A1 | * | 6/2003 | Franklin et al. | 600/407 |
| 2003/0139659 A1 | | 7/2003 | Dale et al. | |
| 2005/0043735 A1 | | 2/2005 | Ahmad | |
| 2006/0147100 A1 | | 7/2006 | Fitzpatrick | |
| 2007/0036402 A1 | | 2/2007 | Cahill et al. | |

OTHER PUBLICATIONS

Bosc et al., "Statistical Atlas-Based Bus-Voxel Segmentation of 3D Brain MRI" {Online} Sep. 14-17, 2003. <htt;://alsace.u-strasbg.fr/ipb/tim/pdf/icip03.pdf> and <http://ieeexplore.ieee.org/xpls/abs$_{13}$all.jsp?arnumber=1246872> entire document.

Matthew Yang Wang, "Fiducial marker recognition and localization for image-guided surgery using point-based registration," Vanderbilt University, May 1998.

Liu, X. et al., "Marker orientation in fiducial registration," Proceedings of SPIE vol. 5032 (2003).

* cited by examiner

*Primary Examiner* — Jacqueline Cheng (74) *Attorney, Agent, or Firm* — Tim Tingkang Xia, Esq.; Morris Manning & Martin, LLP (57) ABSTRACT

In another aspect, the present invention relates to a method for determining the position and orientation of an anchor attached to the skull of a patient from a topographic image of the anchor acquired therefrom. In one embodiment, the method includes the steps of simulating an image of the anchor that matches the acquired topographic image of the anchor, determining the position and orientation of the anchor from the simulated image of the anchor, and determining the position and orientation of the anchor in the acquired topographic image of the anchor from the position and orientation of the anchor determined from the simulated image of the anchor. The simulating step comprises the step of modeling the anchor with an object that has a geometric shape simpler than that of the anchor.

20 Claims, 6 Drawing Sheets

SYSTEM AND METHODS FOR DETERMINING THE ORIENTATION AND POSITION OF A BONE-IMPLANTED ANCHOR

CROSS-REFERENCE TO RELATED PATENT APPLICATION

This application claims the benefit, pursuant to 35 U.S.C. §119(e), of provisional U.S. Patent Application Ser. No. 60/902,735, filed Feb. 22, 2007 entitled "System and methods for determining the orientation of a bone-implanted anchor" by J. Michael Fitzpatrick, the disclosure for which is hereby incorporated herein in its entirety by reference.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [2] represents the 2nd reference cited in the reference list, namely, X. Liu, H. Cevikalp, J. M. Fitzpatrick, "Marker orientation in fiducial registration", Proc. SPIE Medical Imaging 2003, San Diego, Calif., vol. 5032, 1176-1185 (February 2003).

FIELD OF THE INVENTION

The present invention generally relates to determination of the orientation and position of an anchor, and in particular to the determination of the orientation and position of an anchor that is implanted to the skull of a patient to facilitate positioning a platform in connection with an image guidance system for brain surgery.

COPYRIGHT NOTICE

A portion of the disclosure of this patent document contains material which is subject to copyright protection. The copyright owner has no objection to the facsimile reproduction by anyone of the patent document or patent disclosure as it appears in the U.S. Patent and Trademark Office patent file or records, but otherwise reserves all copyright rights whatsoever.

BACKGROUND OF THE INVENTION

Neurosurgeons sometimes rely on "image-guidance" systems to help them navigate through the brain of a patient during a brain surgery. Such an image-guidance system must be positioned in as accurate as possible in relation to a predetermined portion of the patient.

Figure 3:
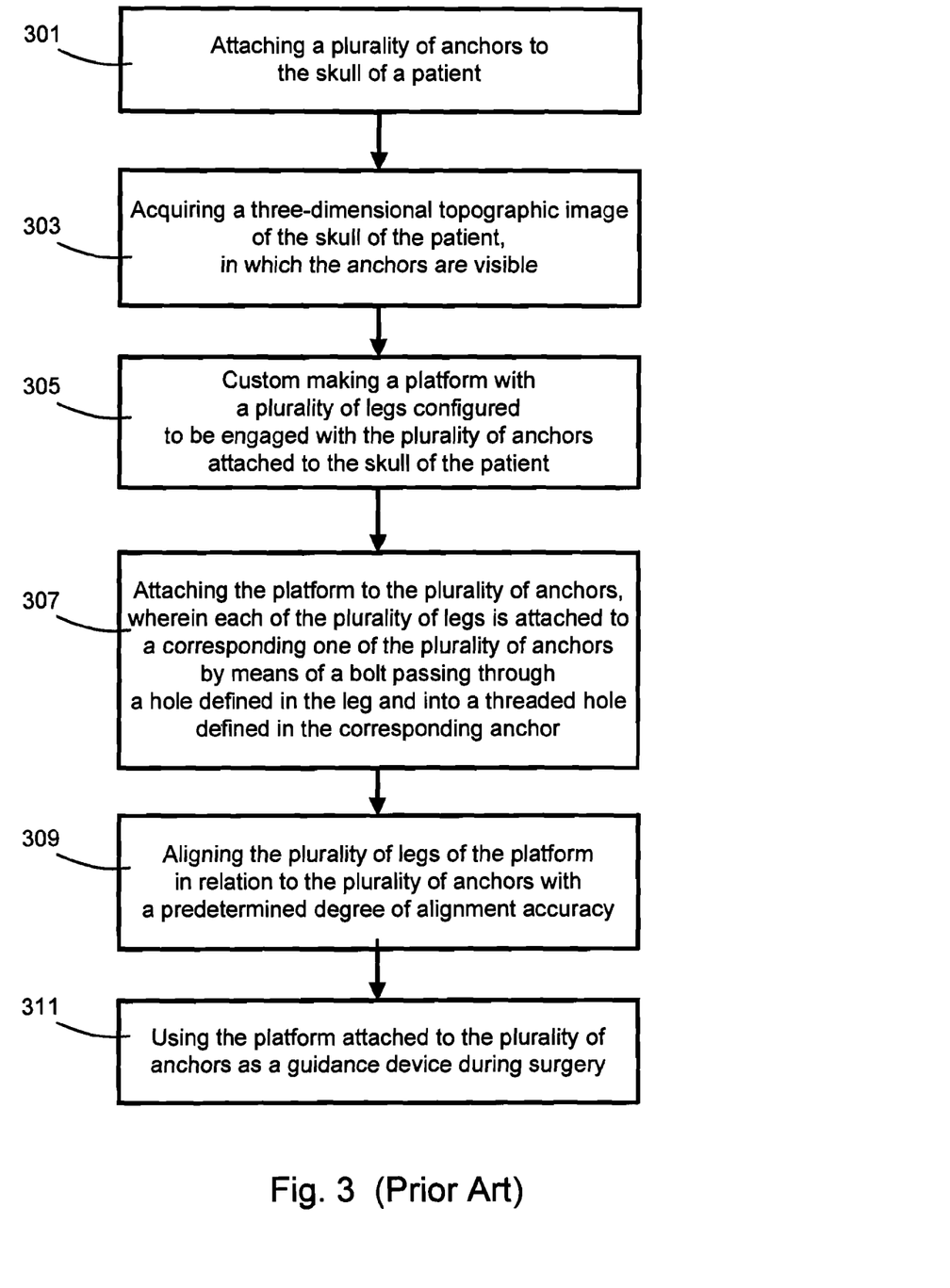
FIG. 3 shows a flow chart of positioning a platform shown in FIG. 2 as a guidance device during a surgery in prior art.

A currently available image-guidance system can be utilized in an operating room in a manner as shown in FIG. 3. First, at step 301, a plurality of anchors is attached to the skull of a patient. At step 303, a three-dimensional (3D) topographic image, such as by x-ray computed tomography (CT), of the skull of the patient is acquired, in which the anchors are visible. At step 305, a platform is customizedly designed and constructed with a plurality of legs to be engaged with the plurality of anchors attached to the skull of the patient, where each of the plurality of legs can be attached by means of a bolt to a corresponding one of the plurality of anchors. At step 307, the platform is attached to the plurality of anchors, wherein each of the plurality of legs is attached to a corresponding one of the plurality of anchors by means of a bolt passing through a hole defined in the leg and into a threaded hole in the corresponding anchor. At step 309, the plurality of legs of the platform is aligned in relation to the plurality of anchors with a predetermined degree of alignment accuracy. And then at step 311, the platform, which is now attached or mounted to the plurality of anchors, is used as a guidance device during surgery.

Figure 1:
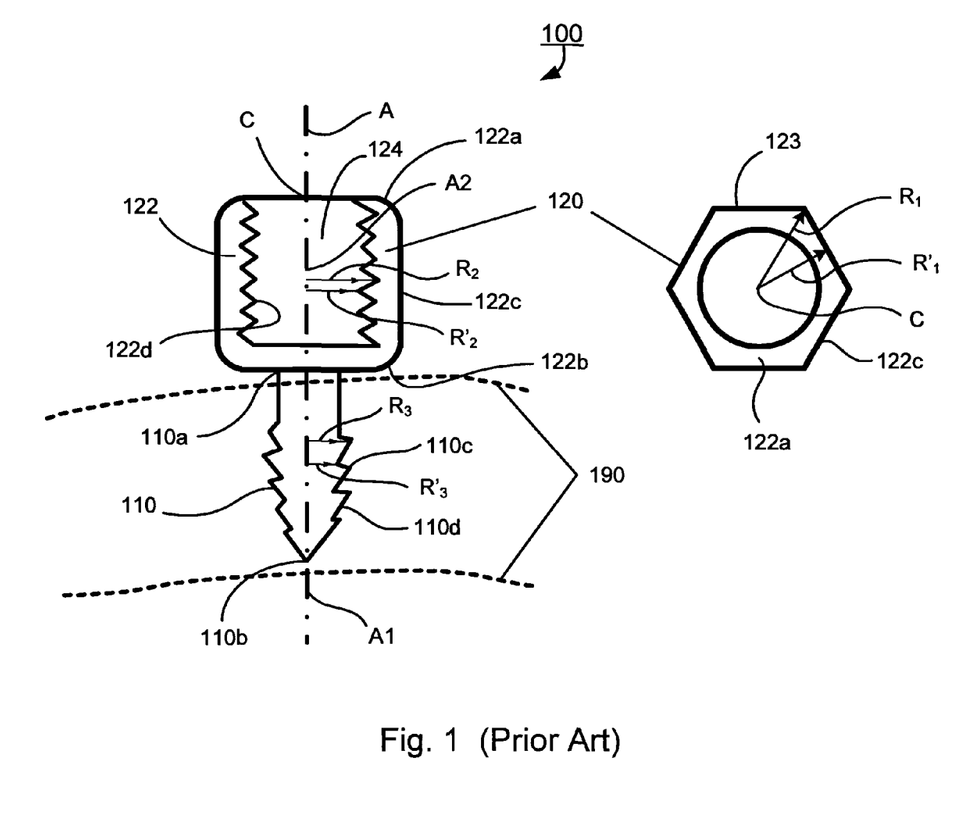
FIG. 1 shows an anchor threaded into an anatomical structure of a patient, which however can be utilized to practice the present invention.
Figure 2:
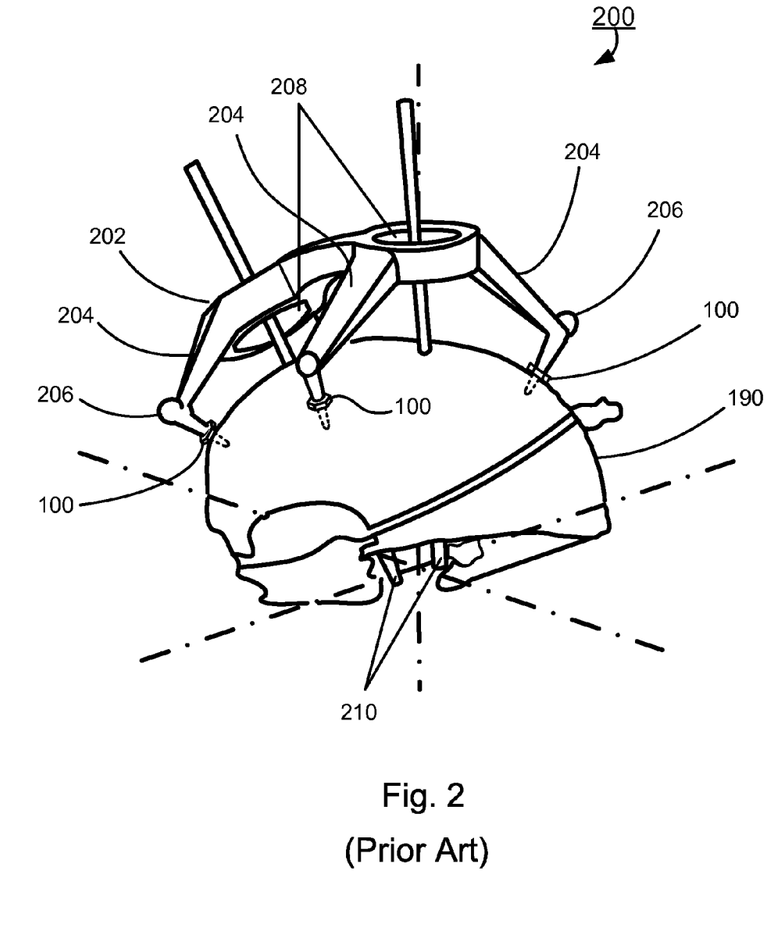
FIG. 2 shows a schematic of an image guiding system attached to a skull through several anchors shown in FIG. 1.

Different types of anchor and platform have been utilized by people skilled in the art. FIGS. 1 and 2 show schematically an exemplary anchor 100 and an exemplary platform 200 mounted to several anchors 100, respectively. As shown in FIG. 1, the anchor 100 has an axis, A, of symmetry representing the orientation of the anchor 100. The anchor 100 also has a cylindrical engagement portion 110 attachable to the skull 190 of a patient, which has an axis, A1, of symmetry representing the orientation of the cylindrical engagement portion 110. And the anchor 100 has a base portion 120 extending away from the cylindrical engagement portion 110 along the axis A, where the base portion 120 has a body 122 defining a threaded recess 124 therein and having an axis, A2, of symmetry representing the orientation of the threaded recess 124, and wherein the axis A1 and the axis A2 are substantially coincident with the axis A. The base portion has a first end 122a (top surface) and an opposite, second end 122b defining the body 122 therebetween, the body 122 has an outer side surface 122c, and an interior surface 122d, where the interior surface 122d is formed in the form of a female threaded portion, and the engagement portion 110 has a first end 110a and an opposite, second end 110b defining a body portion 110c therebetween, the body portion 110c having an outer surface 110d. In this example, the cylindrical engagement portion 110 is in the form of a screw, which attaches the anchor 100 to the skull 190, and the base portion is in the form of a hexagonal nut.

The platform 200 has a frame 202, and several legs 204. This exemplary platform 200 has four legs, although only three of them are shown. But a platform that has other numbers of legs can also be used. A bolt 206 attaches one leg 204 of the platform 200 to a corresponding anchor 100, where the bolt 206 is received into the threaded recess 124. As mounted, the bottom of the leg 204 sits on the top surface of the corresponding anchor 100. The design of the platform permits the bolt to pass through the hole in each leg and into a threaded hole in the corresponding anchor. The platform 200 also has one or more guide holes 208 formed such that a probe 210 attached to them can reach a desired target or targets.

The attachment of the platform 200 to the several anchors 100 requires that both the position of the top center, C, of the threaded recess or hole 124 and the orientation of that hole be determined for every anchor. In practice, these platforms are customized for each patient so that a particular platform can be positioned on a corresponding patient's head to mate with the anchors, which are attached to the skull of the patient at predetermined positions, chosen by medical professionals according to a surgery plan made for that patient. As shown in FIG. 2, the positions and orientations of the anchors, and hence the positions and orientations of their threaded recesses or holes for receiving bolts, are arbitrary. This arbitrariness arises because the positions and orientations depend on the shape of the patient's head, which is varied from one patient to another, and because the locations of the anchors on the head of a particular patient are chosen by the surgeon according to the particular case. The platform must be manufactured so that the holes in its legs line up with the threaded recesses or holes in the anchors to allow a bolt to pass through the hole in the leg and into the threaded recess or hole in the anchor. The platform must be aligned in relation to the anchors to a required alignment accuracy, which is estimated to be on the order of +/−5 degrees, so that bolts can be accurately positioned in right orientation and right position to mount the platform to the anchors, which at least requires two pieces of information: the position of the top center of the anchor hole and the orientation of the hole. The alignment accuracy requirement is estimated to be on the order of +/−5 degrees. These two pieces of information: the position of the top center of the threaded recesses or hole of the anchor and the orientation of the threaded recesses or hole of the anchor, which can be roughly determined by a user who uses interactive graphic software. However, it is difficult to achieve 5-degree accuracy and it is also time consuming for a medical professional to do so in the OR.

Therefore, a heretofore unaddressed need exists in the art to address the aforementioned deficiencies and inadequacies.

SUMMARY OF THE INVENTION

In one aspect, the present invention relates to a method for determining the position and orientation of an anchor attached to the skull of a patient. In one embodiment, the method includes the steps of acquiring a topographic image of the anchor attached to the skull of the patient, simulating an image of the anchor that matches the acquired topographic image of the anchor, determining the position and orientation of the anchor from the simulated image of the anchor, and determining the position and orientation of the anchor in the acquired topographic image of the anchor from the position and orientation of the anchor determined from the simulated image of the anchor.

The anchor has an axis, A, of symmetry representing the orientation of the anchor, a cylindrical engagement portion attachable to the skull of a patient and having an axis, A1, of symmetry representing the orientation of the cylindrical engagement portion, and an base portion extending away from the cylindrical engagement portion along the axis A, wherein the base portion has a body defining a threaded recess therein and having an axis, A2, of symmetry representing the orientation of the threaded recess, and wherein the axis A1 and the axis A2 are substantially coincident with the axis A.

In one embodiment, the simulating step comprises the step of modeling the anchor with a first, second and third cylinders such that the first, the second and the third cylinders are coaxially aligned along the axis A, and wherein the first cylinder represents the base portion, the second cylinder represents the threaded recess, and the third cylinder represents the cylindrical engagement portion of the anchor, respectively, in the acquired topographic image of the anchor.

The simulating step further comprises the step of setting the first cylinder with a first intensity, the second cylinder with a second intensity, and the third cylinder with a third intensity, respectively, wherein the first, the second and the third intensities are respectively corresponding to the intensities of the base portion, the threaded recess and the cylindrical engagement portion of the anchor expected in a topographic image for a material with which the base portion, the threaded recess and the cylindrical engagement portion of the anchor consist of.

In one embodiment, the anchor is formed with one material, wherein the first and third intensities are set identical to each other and corresponding to that of the one material in the topographic image, and wherein the second intensity is corresponding to that of air in the topographic image.

The determining step comprises the steps of matching the simulated image of the anchor onto the acquired topographic image of the anchor, and determining the orientation of the threaded recess and the position of a top center of the base portion of the anchor from the position and orientation of the anchor determined from the simulated image of the anchor, so as to determining the orientation and the position of the anchor.

The step of matching of the simulated image to the actual image of an anchor is performed with an optical flow registration algorithm.

The topographic image comprises a computed topographic (CT) image, or a magnetic resonance (MR) image.

In another aspect, the present invention relates to a method for determining the position and orientation of an anchor attached to the skull of a patient from a topographic image of the anchor acquired therefrom. In one embodiment, the method includes the steps of simulating an image of the anchor that matches the acquired topographic image of the anchor, determining the position and orientation of the anchor from the simulated image of the anchor, and determining the position and orientation of the anchor in the acquired topographic image of the anchor from the position and orientation of the anchor determined from the simulated image of the anchor. The simulating step comprises the step of modeling the anchor with an object that has a geometric shape simpler than that of the anchor. Note that it is not necessary to simplify every part of the anchor in the modeling to practice the present invention, depending on the original geometric shape of anchor to be used.

In yet another aspect, the present invention relates to a system for determining the position and orientation of an anchor attached to the skull of a patient from a topographic image of the anchor acquired therefrom. In one embodiment, the system has a controller configured to perform the steps of simulating an image of the anchor that matches the acquired topographic image of the anchor, determining the position and orientation of the anchor from the simulated image of the anchor, and determining the position and orientation of the anchor in the acquired topographic image of the anchor from the position and orientation of the anchor found from the simulated image of the anchor. The system can also have means for acquiring the topographic image.

In a further aspect, the present invention relates to a method for positioning a platform of an image-guidance system in relation to the skull of a patient. In one embodiment, the method can be practiced in the following manner: first, a plurality of anchors, $\{a_i\}$, $i=1, \ldots, N$, N being an integer greater than one, are attached to the skull of a patient. Then, a topographic image is acquired for each of the plurality of anchors $\{a_i\}$, where the image of the anchors should be visible. An image of the anchor $a_i$ that matches the acquired topographic image of the anchor $a_i$ is simulated, which includes the step of modeling the anchor $a_i$ with a corresponding object that has a geometric shape simpler than that of the anchor $a_i$. Then, the position and orientation of the anchor $a_i$ from the simulated image of the anchor $a_i$ are determined. The position and orientation of the anchor $a_i$ in the acquired topographic image of the anchor $a_i$ are determined from the position and orientation of the anchor $a_i$ determined from the simulated image of the anchor $a_i$. These relevant steps are repeated for each and every one of the plurality of anchors, $\{a_i\}$, $i=1, \ldots, N$ to obtain the position and orientation for each and every one of the plurality of anchors $\{a_i\}$ in the acquired topographic image. Finally, the obtained information of the position and orientation for each and every one of the plurality of anchors $\{a_i\}$ is used to attach and align a corresponding platform to the plurality of anchors $\{a_i\}$.

In yet another aspect, the present invention relates to a system for positioning a platform of an image-guidance system in relation to the skull of a patient. In one embodiment, the system has a controller configured to perform the steps of (a) attaching a plurality of anchors, $\{a_i\}$, i=1, . . . , N, N being an integer greater than one, to the skull of a patient, (b) acquiring a topographic image for each of the plurality of anchors $\{a_i\}$, (c) simulating an image of the anchor $a_i$ that matches the acquired topographic image of the anchor $a_i$, (d) determining the position and orientation of the anchor $a_i$ from the simulated image of the anchor $a_i$, (e) determining the position and orientation of the anchor $a_i$ in the acquired topographic image of the anchor $a_i$ from the position and orientation of the anchor $a_i$ determined from the simulated image of the anchor $a_i$, (f) repeating steps (b)-(e) for each and every one of the plurality of anchors, $\{a_i\}$, i=1, . . . , N to obtain the position and orientation for each and every one of the plurality of anchors $\{a_i\}$ in the acquired topographic image, and (g) using the obtained position and orientation for each and every one of the plurality of anchors $\{a_i\}$ to attach and align a corresponding platform to the plurality of anchors $\{a_i\}$. When the controller performs the simulating step, it performs the step of modeling the anchor $a_i$ with a corresponding object that has a geometric shape simpler than that of the anchor $a_i$.

These and other aspects of the present invention will become apparent from the following description of the preferred embodiment taken in conjunction with the following drawings, although variations and modifications therein may be affected without departing from the spirit and scope of the novel concepts of the disclosure.

DETAILED DESCRIPTION OF THE INVENTION

The present invention is more particularly described in the following examples that are intended as illustrative only since numerous modifications and variations therein will be apparent to those skilled in the art. Various embodiments of the invention are now described in detail. Referring to the drawings, like numbers indicate like parts throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise.

DEFINITIONS

The terms used in this specification generally have their ordinary meanings in the art, within the context of the invention, and in the specific context where each term is used.

Certain terms that are used to describe the invention are discussed below, or elsewhere in the specification, to provide additional guidance to the practitioner in describing the apparatus and methods of the invention and how to make and use them. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification. Furthermore, subtitles may be used to help a reader of the specification to read through the specification, which the usage of subtitles, however, has no influence on the scope of the invention.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, "centroid" refers to a point that represents the mean position of an anchor.

As used herein, "axis of symmetry" refers to an axis that uniquely represents the orientation of an anchor, or the orientation of a portion or part of an anchor, depending upon the specific context where the term is used.

Overview of the Invention

In accordance with the purposes of this invention, as embodied and broadly described herein, this invention, in one aspect, relates to a method for determining the position and orientation of an anchor attached to an anatomical structure of a patient such as the skull of a patient.

In one embodiment, the method includes the step of acquiring a topographic image of an anchor attached to the skull of the patient. The topographic image can be a computed topographic (CT) image, or a magnetic resonance (MR) image. In the acquired topographic image of the anchor, which can be three-dimensional, the image of the anchor should be visible.

The method further includes the steps of simulating an image of the anchor that matches the acquired topographic image of the anchor, determining the position and orientation of the anchor from the simulated image of the anchor, and determining the position and orientation of the anchor in the acquired topographic image of the anchor from the position and orientation of the anchor determined from the simulated image of the anchor.

In the simulating step, at first, the anchor is modeled with an object that has a geometric shape simpler than that of the anchor. In this modeling, the choice of the object that models the anchor thus depends on, among other things, the geometric shape of the anchor. For example, if the anchor as shown in FIG. 1 is utilized, as set forth above, the anchor 100 has a cylindrical engagement portion 110 that is in the form of a screw, a base portion 120 that is in the form of a hexagonal nut, and an interior surface 122d that is formed in the form of a female threaded portion. Accordingly, for the "real" anchor 100, referring now to FIG. 1, for the base portion 120, the radial distance from the axis A2 to the outer surface 122c of the base portion 120 is varied: for example, the radial distance $R_1$, from the axis A2 to the outer surface 122c of the base portion 120 at one of the six corners of the hexagonal nut, is greater than the radial distance $R_1'$, from the axis A2 to the outer surface 122c of the base portion 120 at a point that is away from the corner. Likewise, for the threaded recess 124, the radial distance from the axis A2 to the interior surface 122d is also varied: the radial distance $R_2$, from the axis A2 to the interior surface 122d of the base portion 120 at a recess of the female threaded portion, is greater than the radial distance $R_2$, from the axis A2 to the interior surface 122d of the base portion 120 at a neighboring cusp of the female threaded portion. Similarly, for the engagement portion 110, the radial distance from the axis A1 to the outer surface 110d is varied: for example, the radial distance $R_3$, from the axis A1 to the outer surface 110d of the engagement portion 110 (i.e., screw) at a cusp of the male threaded portion of the screw, is greater than the radial distance $R_3$, from the axis A2 to the outer surface 110d at a neighboring recess of the male threaded portion of the screw. Thus, the anchor 100 has a rather complicated geometric shape, which poses challenge to the attempt to simulate it in real time.

Figure 4:
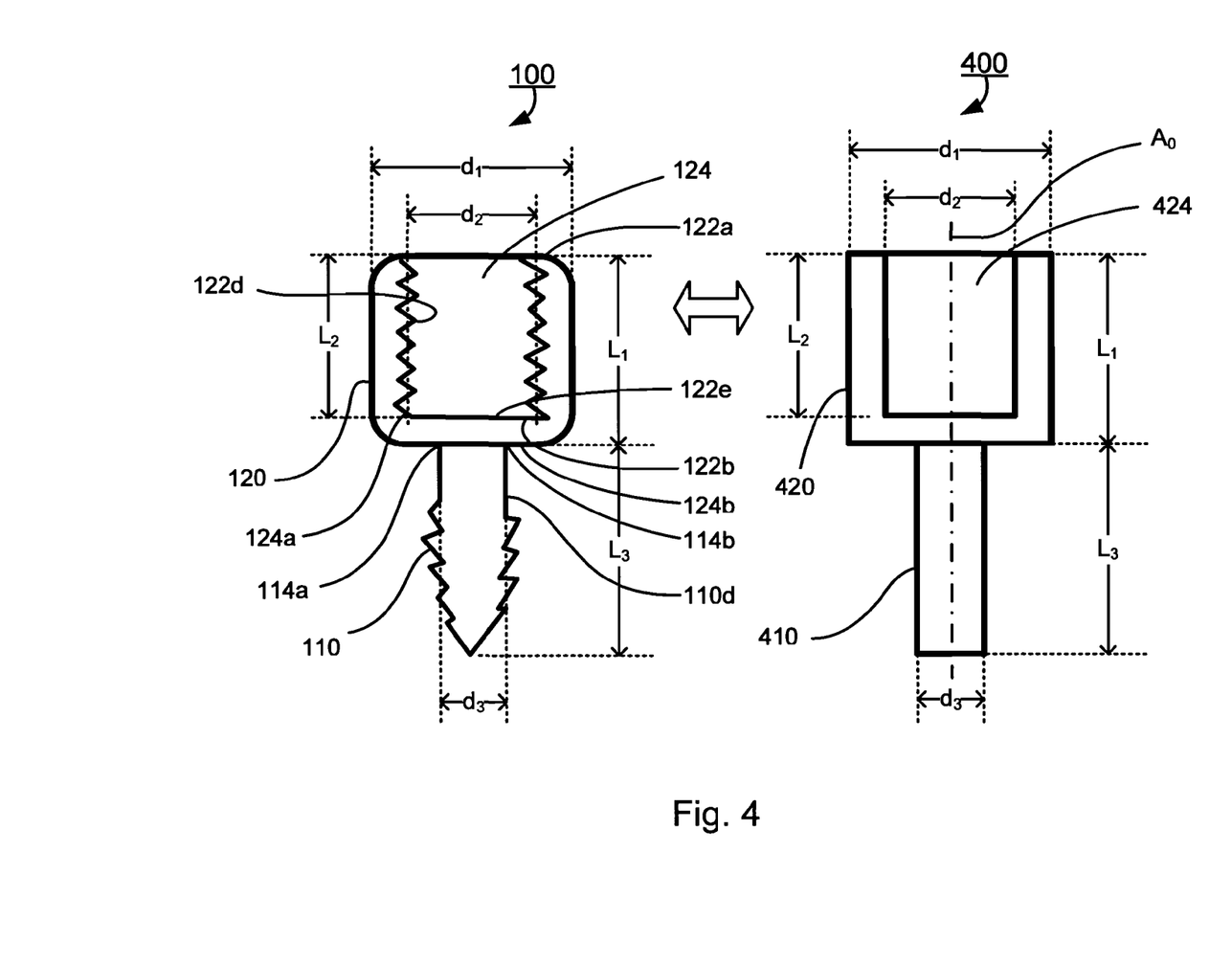
FIG. 4 shows schematically modeling an anchor shown in FIG. 1 with a corresponding object with simpler geometric shape according to one embodiment of the present invention.

In one embodiment of the present invention, the anchor 100 is modeled with a first, second and third cylinders 420, 424, and 410, which are coaxially aligned along the axis A to form an object 400, where the first cylinder 420 represents the base portion 120, the second cylinder 424 represents the threaded recess 124, and the third cylinder 410 represents the cylindrical engagement portion 110 of the anchor 100, respectively, in the acquired topographic image of the anchor 100.

Figure 5:
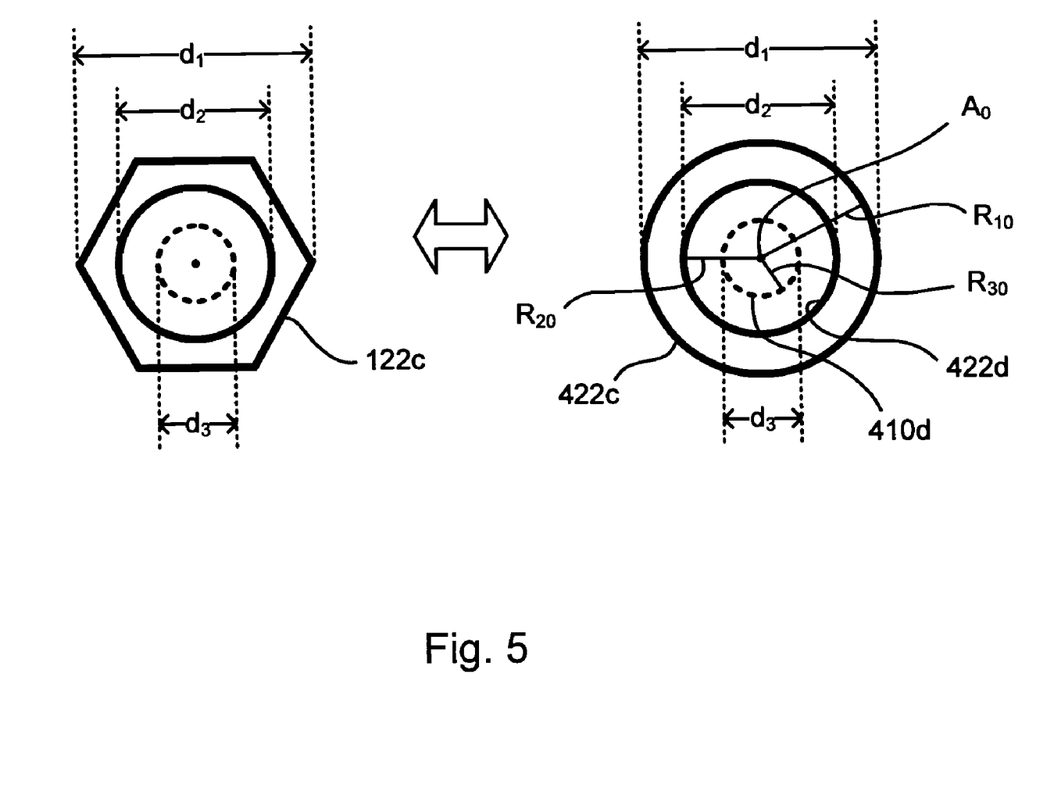
FIG. 5 shows schematically modeling an anchor shown in FIG. 1 with a corresponding object with simpler geometric shape according to one embodiment of the present invention in connection with FIG. 4.

More specifically, referring now to FIG. 4 and FIG. 5, the first cylinder 420 is chosen to have an axial length $L_1$, which is the length between the first end 122a and the second end 122b of the body 122 of the base portion 120, and a radial diameter $d_1$, which is the radial diameter of the body 122 of the base portion 120. As such modeled, the outer surface 122c of the base portion 120, which is hexagonal cross-section-wise and is characterized by a varied "radius" $R_1$, is modeled with an outer surface 422c of the first cylinder 420, which is circular cross-section-wise and is characterized by a constant radius $R_{10}$. In other words, the hexagonal nut is modeled as the first cylinder, which has a geometric shape simpler than that of the hexagonal nut.

Likewise, still referring to FIG. 4 and FIG. 5, the second cylinder 424 is chosen to have an axial length $L_2$, which is the length between the first end 122a of the body 122 of the base portion 120 and the bottom surface 122e of the threaded recess 124, and a radial diameter $d_2$, which is the mean or average radial diameter of the threaded recess 124, measured between a first corner point 124a, and an opposite, second corner point 124b, which are at the opposite intersections of the interior surface 122d and the bottom surface 122e. As such modeled, the interior surface 122d of the base portion 120, which is in the form of a female threaded portion and is characterized by a varied "radius" $R_2$, is modeled with an interior surface 422d of the second cylinder 420, which is circular cross-section-wise and is characterized by a constant radius $R_{20}$. In other words, the threaded recess is modeled as the second cylinder, which has a geometric shape simpler than that of the threaded recess.

Furthermore, also referring to FIG. 4 and FIG. 5, the third cylinder 410 is chosen to have an axial length $L_3$, which is the length between the first end 110a of the body portion 110c of the engagement portion 110 and the second end 110b of the body portion 110c of the engagement portion 110, and a radial diameter $d_3$, which is the mean or average radial diameter of the body portion 110c, measured between a first corner point 114a, and an opposite, second corner point 114b, which are at the opposite intersections of the outer surface 110d of the engagement portion 110 and the second end 122b of the body 122 of the base portion 120. As such modeled, the outer surface 110d of the engagement portion 110, which is in the form of a male threaded portion (or a screw) and is characterized by a varied "radius" $R_3$, is modeled with an outer surface 410d of the third cylinder 410, which is circular cross-section-wise and is characterized by a constant radius $R_{30}$. In other words, the screw is modeled as the third cylinder, which has a geometric shape simpler than that of the screw.

Note that in terms of materials that form the anchor, different parts of the anchor can be made from different materials based on various possible needs, which would generate different intensities in a topographic image. Moreover, a recess in fact is a cavity filled with air, which would generate a different image than an object made from solid material such as a screw. Thus, in one embodiment, in the simulating step, the first cylinder is given or set with a first intensity, the second cylinder is given or set with a second intensity, and the third cylinder is given or set with a third intensity, respectively, wherein the first, the second and the third intensities are respectively corresponding to the intensities of the base portion 120, the threaded recess 124 and the cylindrical engagement portion 110 of the anchor 100 expected in a topographic image for a material with which the base portion 120, the threaded recess 124 and the cylindrical engagement portion 110 of the anchor 100 consist of.

More specifically, for the embodiment as shown in FIGS. 4 and 5, where the anchor 100 is formed with one material such as a metal, the first and third intensities are set identical to each other and corresponding to that of the one material in the topographic image, and the second intensity is corresponding to that of air in the topographic image.

A simulated image of the anchor then can be obtained. Afterwards, the simulated image of the anchor is best matched to the acquired topographic image of the anchor. Once the best match is found, the position and orientation of the simulated anchor can be determined from the best matched, simulated image of the anchor. Then, the orientation of the threaded recess 124 and the position of a top center C of the base portion of the anchor 100 or the centroid of the anchor 100 can be chosen as the position and orientation of the simulated anchor determined from the simulated image of the anchor, which also determines the orientation and the position of the anchor 100.

In one embodiment, the step of matching of the simulated image to the actual image of an anchor is performed with an optical flow registration algorithm as known to people skilled in the art, which, and other tasks of this inventive method, can be performed by using a controller associated with a computer.

Once the orientation and the position of one anchor 100 are obtained, the procedure is repeated for each of the rest of the anchors until the orientation and the position of each and every anchor that is to be used to position the platform are obtained. Then a corresponding platform is aligned and attached to the plurality of anchors, which has total number of four (4) for the example shown in FIG. 2, by using the information related to the orientation and the position of each and every anchor obtained from the simulated image.

In another aspect, the present invention relates to a method for determining the position and orientation of an anchor attached to the skull of a patient from a topographic image of the anchor acquired therefrom. In one embodiment, the method includes the steps of simulating an image of the anchor that matches the acquired topographic image of the anchor, determining the position and orientation of the anchor from the simulated image of the anchor, and determining the position and orientation of the anchor in the acquired topographic image of the anchor from the position and orientation of the anchor determined from the simulated image of the anchor. The simulating step comprises the step of modeling the anchor with an object that has a geometric shape simpler than that of the anchor. Note that it is not necessary to simplify every part of the anchor in the modeling to practice the present invention, depending on the original geometric shape of anchor to be used.

In yet another aspect, the present invention relates to a system for determining the position and orientation of an anchor attached to the skull of a patient from a topographic image of the anchor acquired therefrom. In one embodiment, the system has a controller configured to perform the steps of simulating an image of the anchor that matches the acquired topographic image of the anchor, determining the position and orientation of the anchor from the simulated image of the anchor, and determining the position and orientation of the anchor in the acquired topographic image of the anchor from the position and orientation of the anchor found from the simulated image of the anchor. The system can also have means for acquiring the topographic image.

Figure 6:
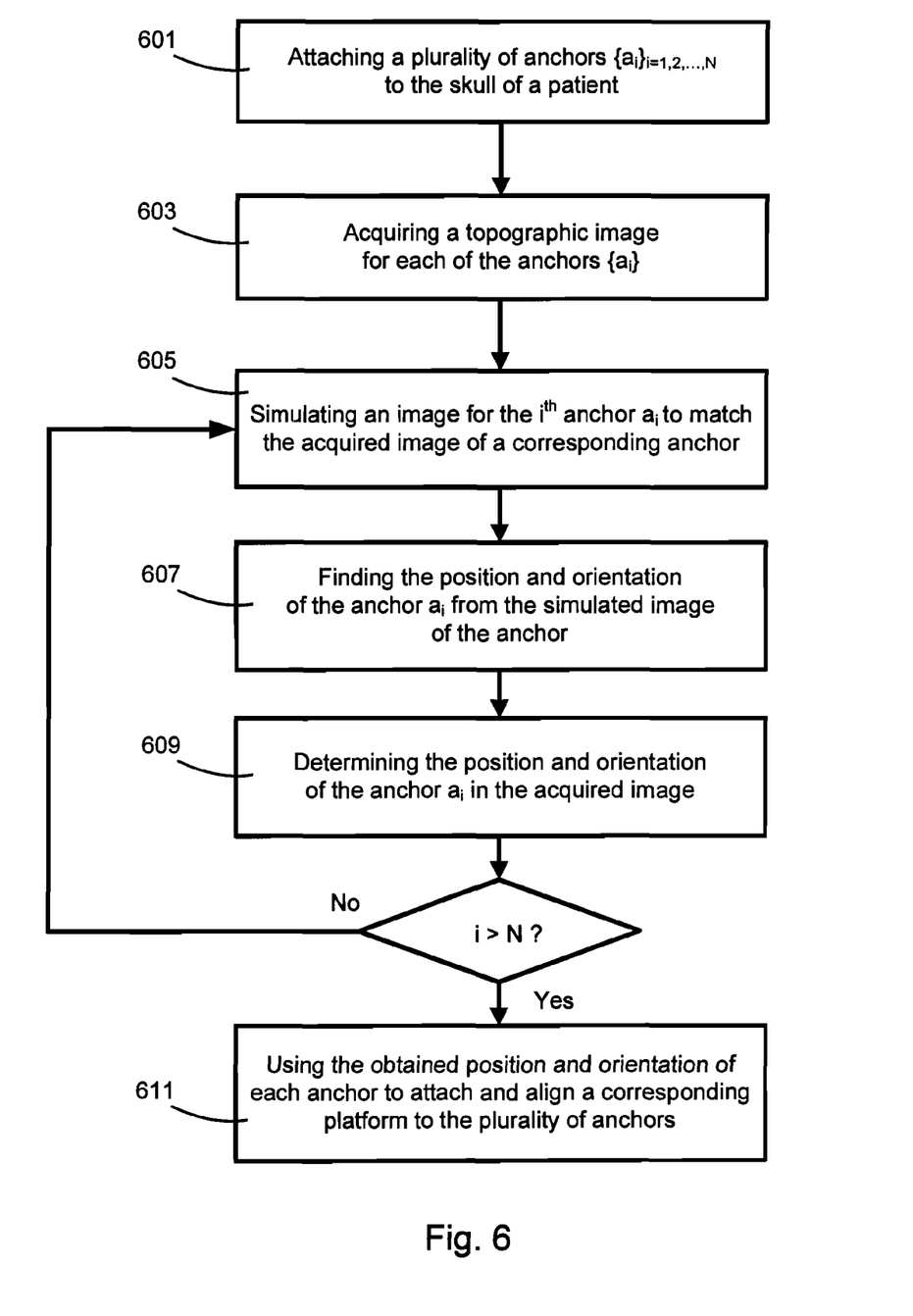
FIG. 6 shows a flow chart of positioning a platform as a guidance device during a surgery according to one embodiment of the present invention.

In a further aspect, the present invention relates to a method for positioning a platform of an image-guidance system in relation to the skull of a patient. In one embodiment, referring to FIG. 6, the method can be practiced in the following manner. At step 601, a plurality of anchors, $\{a_i\}$, $i=1, \ldots, N$, N being an integer greater than one, are attached to the skull of a patient. For the platform shown in FIG. 2, N would be four (4). At step 603, a topographic image is acquired for each of the plurality of anchors $\{a_i\}$ where the image of the anchors should be visible. In practice, one may just need to acquire fewer than N topographic images to have enough information to proceed. At step 605, an image of the anchor $a_i$ that matches the acquired topographic image of the anchor $a_i$ is simulated. As set forth above for the exemplary anchor 100, performing the simulating step includes the step of modeling the anchor $a_i$ with a corresponding object that has a geometric shape simpler than that of the anchor $a_i$. At step 607, the position and orientation of the anchor $a_i$ from the simulated image of the anchor $a_i$ are determined. At step 609, the position and orientation of the anchor $a_i$ in the acquired topographic image of the anchor $a_i$ are determined from the position and orientation of the anchor $a_i$ determined from the simulated image of the anchor $a_i$. Then, steps 605-609 are repeated for each and every one of the plurality of anchors, $\{a_i\}$, $i=1, \ldots, N$ to obtain the position and orientation for each and every one of the plurality of anchors $\{a_i\}$ in the acquired topographic image. Finally, at step 611, the obtained information of the position and orientation for each and every one of the plurality of anchors $\{a_i\}$ is used to attach and align a corresponding platform to the plurality of anchors $\{a_i\}$.

In yet another aspect, the present invention relates to a system for positioning a platform of an image-guidance system in relation to the skull of a patient. In one embodiment, the system has a controller configured to perform the steps of (a) attaching a plurality of anchors, $\{a_i\}$, $i=1, \ldots, N$, N being an integer greater than one, to the skull of a patient, (b) acquiring a topographic image for each of the plurality of anchors $\{a_i\}$, (c) simulating an image of the anchor $a_i$ that matches the acquired topographic image of the anchor $a_i$, (d) determining the position and orientation of the anchor $a_i$ from the simulated image of the anchor $a_i$, (e) determining the position and orientation of the anchor $a_i$ in the acquired topographic image of the anchor $a_i$ from the position and orientation of the anchor $a_i$ determined from the simulated image of the anchor $a_i$, (f) repeating steps (b)-(e) for each and every one of the plurality of anchors, $\{a_i\}$, $i=1, \ldots, N$ to obtain the position and orientation for each and every one of the plurality of anchors $\{a_i\}$ in the acquired topographic image, and (g) using the obtained position and orientation for each and every one of the plurality of anchors $\{a_i\}$ to attach and align a corresponding platform to the plurality of anchors $\{a_i\}$. When the controller performs the simulating step, it performs the step of modeling the anchor $a_i$ with a corresponding object that has a geometric shape simpler than that of the anchor $a_i$.

EXAMPLES

Still using the anchor 100 shown in FIG. 1 as an example.

In one embodiment, the method includes the following steps: at first, an image of the anchor is acquired from the anatomical structure of the patient. The acquired topographic image includes a topographic image. The topographic image includes a computed topographic (CT) image, or a magnetic resonance (MR) image.

Second, an image of the anchor is simulated that best matches the acquired topographic image of the anchor. For the purpose of modeling an anchor to produce a simulated image, the anchor has approximate cylindrical symmetry. However, as shown in FIG. 1, the top of the anchor 100 has a hexagonal outer shape 123 to accommodate a driver when it is screwed (threaded) into the anatomical structure 190, such as skull, of a human. The hexagonal shape 123 can be approximated as a cylinder for the purposes of simulating an image. Furthermore, the helical threads in the recess (hole) 124 and on the engagement portion 110 which is screwed into the skull, can be ignored. These differences from the cylindrical symmetry are small relative to the size of the voxels used in a typical CT image (around 0.5×0.5×1 mm), and thus ignoring them will not have an appreciable effect on the image. It also reduces the time for simulation required by a computer.

The simulating step in one embodiment includes the step of modeling the anchor with a first, second and third cylinders such that the first to third cylinders are coaxially aligned alone the axis A1 and match the base portion, the threaded recess and the engagement portion of the anchor, respectively, in the acquired topographic image of the anchor. The simulating step further includes the step of setting the first to third cylinders with first to third intensities, respectively, wherein the first to third intensities are respectively corresponding to the intensities of the base portion, the threaded recess and the engagement portion of the anchor expected in a topographic image for materials with which the base portion, the threaded recess and the engagement portion of the anchor are formed. In one embodiment, the anchor is formed with a single, imagable material, such as titanium. Accordingly, the first and second intensities are identical and corresponding to that of the single material in the topographic image, and wherein the second intensity is corresponding to that of air in the topographic image, where the intensity of air in a standard CT is about 1,000.

Then, the position and orientation of the anchor are found from the simulated image of the anchor. And next, the position and orientation of the anchor in the acquired topographic image of the anchor are determined from the position and orientation of the anchor found from the simulated image of the anchor.

In one embodiment, the determining step comprises the steps of matching the simulated image of the anchor onto the acquired topographic image of the anchor; and determining the orientation of the threaded recess and the position of the center of the base portion of the anchor from the position and orientation of the anchor found from the simulated image of the anchor, so as to determining the orientation and the position of the anchor.

The matching of the simulated image to the acquired topographic image of an anchor can be done by altering an existing algorithm [1, 2] so that it gives the anchor orientation and anchor centroid. This algorithm utilizes an optic flow method for matching a model of an object to the image of that object. The previous version of the software, while it iteratively estimates a better and better orientation of the marker, uses those orientations internally only as a means for determining an accurate estimate for the position of the marker's centroid. In this embodiment, both the centroid and the orientation are recorded at each step. After a number of iterations (typically ranging from 3 to 15) of the optic-flow implementation, the final orientation and centroid are recorded. The optic-flow algorithm requires a preprocessing stage that determines both an approximate centroid and an approximate orientation. In one embodiment of the present invention, this step is carried out by means of an alternative algorithm, designed and implemented in computer code by the inventor, which is set forth below, Note that in this embodiment, the anchor is made from Titanium, and the relevant parameters for the anchor are:

$L_1$=3.86 mm, $L_2$=3.48 mm, $L_3$=4.01 mm,
$d_1$=4.00 mm, $d_2$=3.00 mm, and $d_3$=1.30 mm.

The resulting determination of the orientation of the threaded hole and of its top center is likely to be more accurate if, instead of focusing on only the hole itself (i.e., a single cylinder of CT intensity equal to that of air), the entire anchor is modeled. That is what the invention does. It creates a simulated image based on a model of the entire anchor, fits that image to the actual image, and then determines the orientation of the actual hole and the position of the actual top center from the best-fit orientation of the model of the entire anchor, the position of the center of the anchor (as opposed to its top center) and the distance along the axis of symmetry of the from the anchor center to the top of the hole.

The algorithm has implemented in computer code and tested in phantoms and patient images.

While there has been shown various embodiments of the present invention, it is to be understood that certain changes can be made in the form and arrangement of the elements of the apparatus and steps of the methods to practice the present invention as would be known to one skilled in the art without departing from the underlying scope of the invention as is particularly set forth in the Claims. For examples, while examples set forth above are related to practice the present invention for cylindrical anchors, the present invention can be practiced for other shapes of anchors as well. Furthermore, the embodiments described above are only intended to illustrate the principles of the present invention and are not intended to limit the claims to the disclosed elements.

REFERENCES LIST

[1] Matthew Y. Wang, "Fiducial Marker Recognition and Localization for Image-Guided surgery Using Point-Based Registration", Ph.D., Computer Science (May 1998).

```
TITANIUM_ANCHOR_CT: begin ; Titanium anchor in CT
    MARKER_DIAMETER = 4.00D ;(mm) the volume inside the marker (excludes the plastic)
    MARKER_HEIGHT = 5.00D ; ;(mm) the volume inside the marker (excludes the plastic)
    FIDUCIAL_STANDOFF = 0.0D; (mm) distance from centroid to fiducial point (positive is
toward air)
    MARKER_EXTENT = norm([MARKER_DIAMETER,MARKER_HEIGHT]); longest
dimension of marker
    MARKER_VOLUME = !dpi*(MARKER_DIAMETER/2)^2*MARKER_HEIGHT; in mm-
cubed; !dpi = double precision value of pi
    EXTENT_VOXELS = MARKER_EXTENT/voxel_size + 2; longest distance between
voxels that intersect marker
    MAX_SENSE_DISTANCE = 50.0D; distance (mm) to explore when determining the sense
of the symmetry axis
    MARKER_MOMENT_RATIO =
(MARKER_HEIGHT^2/12+MARKER_DIAMETER^2/16)/(MARKER_DIAMETER^2/8); see
Medim 2003.
    MAX_INTENSITY = 4095.0D; ; the intensity at which the CT clips
    EMPTY_INTENSITY = 0.0D;   ; the intensity of an empty voxel (= minimum intensity
produced by scanner)
    MARKER_INTENSITY = 3900D; ; potential intensity of a voxel of marker material
without clipping
    FIRST_THRESHOLD_FRACTION = 0.90D ;
    SECOND_THRESHOLD_FRACTION = 0.80D ;
    FIRST_THRESHOLD =
FIRST_THRESHOLD_FRACTION*min([MAX_INTENSITY,MARKER_INTENSITY]);
    SECOND_THRESHOLD =
SECOND_THRESHOLD_FRACTION*min([MAX_INTENSITY,MARKER_INTENSITY]);
    VOLUME_FRACTION_MIN = 0.85D ; as compared to analytical formula
    VOLUME_FRACTION_MAX = 1.25D ; as compared to analytical formula
    RATIO_DIFF_MAX = 1.0D ; i.e., max allowed difference of ratio (sic) of moments of
inertia
    end
```

[2] X. Liu, H. Cevikalp, J. M. Fitzpatrick, "Marker orientation in fiducial registration", Proc. SPIE Medical Imaging 2003, San Diego, Calif., vol. 5032, 1176-1185 (February 2003).

What is claimed is:

1. A method for determining the position and orientation of an anchor attached to the skull of a patient, comprising the steps of:
   acquiring a topographic image of the anchor and the skull;
   defining a physical model of the anchor independently of the topographic image acquired;
   simulating an image of the anchor based on the physical model;
   matching the simulated image of the anchor onto the acquired topographic image;
   determining the position and orientation of the anchor in the simulated image of the anchor; and
   determining the position and orientation of the anchor in the acquired topographic image based on the matching and the determined position and orientation of the anchor in the simulated image of the anchor.

2. The method of claim 1, wherein the anchor has an axis, A, of symmetry representing the orientation of the anchor, a cylindrical engagement portion attachable to the skull of a patient and having an axis, A1, of symmetry representing the orientation of the cylindrical engagement portion, and a base portion extending away from the cylindrical engagement portion along the axis A, wherein the base portion has a body defining a threaded recess therein and having an axis, A2, of symmetry representing the orientation of the threaded recess, and wherein the axis A1 and the axis A2 are substantially coincident with the axis A.

3. The method of claim 1, wherein the topographic image comprises a computed topographic (CT) image, or a magnetic resonance (MR) image.

4. A method for determining the position and orientation of an anchor attached to the skull of a patient, comprising the steps of:
   (a.) acquiring a topographic image of the anchor attached to the skull of the patient;
   (b.) simulating an image of the anchor that matches the acquired topographic image of the anchor;
   (c.) determining the position and orientation of the anchor from the simulated image of the anchor; and
   (d.) determining the position and orientation of the anchor in the acquired topographic image of the anchor from the position and orientation of the anchor determined from the simulated image of the anchor,
   wherein the anchor has an axis, A, of symmetry representing the orientation of the anchor, a cylindrical engagement portion attachable to the skull of a patient and having an axis, A1, of symmetry representing the orientation of the cylindrical engagement portion, and a base portion extending away from the cylindrical engagement portion along the axis A, wherein the base portion has a body defining a threaded recess therein and having an axis, A2, of symmetry representing the orientation of the threaded recess, and wherein the axis A1 and the axis A2 are substantially coincident with the axis A,
   wherein the simulating step comprises a step of modeling the anchor with a first, second and third cylinders such that the first, the second and the third cylinders are coaxially aligned along the axis A, and wherein the first cylinder represents the base portion, the second cylinder represents the threaded recess, and the third cylinder represents the cylindrical engagement portion of the anchor, respectively, in the acquired topographic image of the anchor.

5. The method of claim 4, wherein the simulating step further comprises a step of setting the first cylinder with a first intensity, the second cylinder with a second intensity, and the third cylinder with a third intensity, respectively, wherein the first, the second and the third intensities are respectively corresponding to the intensities of the base portion, the threaded recess and the cylindrical engagement portion of the anchor expected in a topographic image for a material with which the base portion, the threaded recess and the cylindrical engagement portion of the anchor consist of.

6. The method of claim 5, wherein the anchor is formed with one material.

7. The method of claim 6, wherein the first and third intensities are set identical to each other and corresponding to that of the one material of the anchor in the topographic image, and wherein the second intensity is corresponding to that of air in the topographic image.

8. The method of claim 5, wherein the determining step comprises the steps of
   (a.) matching the simulated image of the anchor onto the acquired topographic image of the anchor; and
   (b.) determining the orientation of the threaded recess and the position of a top center of the base portion of the anchor from the position and orientation of the anchor determined from the simulated image of the anchor, so as to determining the orientation and the position of the anchor.

9. The method of claim 8, wherein the step of matching of the simulated image to the actual image of an anchor is performed with an optical flow registration algorithm.

10. A method for determining the position and orientation of an anchor attached to the skull of a patient from a topographic image of the anchor acquired therefrom, comprising the steps of:
   a. simulating an image of the anchor that matches the acquired topographic image of the anchor;
   b. determining the position and orientation of the anchor from the simulated image of the anchor; and
   c. determining the position and orientation of the anchor in the acquired topographic image of the anchor from the position and orientation of the anchor determined from the simulated image of the anchor;
   wherein the anchor has an axis, A, of symmetry representing the orientation of the anchor, an engagement portion attachable to the skull of a patient and having an axis, A1, of symmetry representing the orientation of the engagement portion, and a base portion extending away from the engagement portion along the axis A, wherein the base portion has a body defining a recess therein and having an axis, A2, of symmetry representing the orientation of the recess, and wherein the axis A1 and the axis A2 are substantially coincident with the axis A;
   wherein the base portion has a first end and an opposite, second end defining the body therebetween, the body has an outer side surface, wherein the radial distance from the axis A2 to the outer side surface is varied, and an interior surface, wherein the radial distance from the axis A2 to the interior surface is varied, and the engagement portion has a first end and an opposite, second end defining an engagement body portion therebetween, the engagement body portion having an engagement outer surface, wherein the radial distance from the axis A1 to the engagement outer surface is varied;

wherein the simulating step comprises a step of modeling the anchor with an object that has a geometric shape simpler than that of the anchor.

11. The method of claim 10, wherein the geometric shape of the object is modeled to have a central axis, a radial axis perpendicular to the central axis, and an outer surface such that the radial distance from the central axis to the outer surface is constant, and wherein the object at least represents one of the base portion, the recess, and the engagement portion of the anchor.

12. The method of claim 11, wherein the object comprises a first, second and third cylinders, and the modeling step comprises the step of modeling the anchor with the first, second and third cylinders such that the first, the second and the third cylinders are coaxially aligned along the axis A, and wherein the first cylinder represents the base portion, the second cylinder represents the recess, and the third cylinder represents the engagement portion of the anchor, respectively.

13. The method of claim 12, wherein the simulating step further comprises a step of setting the first cylinder with a first intensity, the second cylinder with a second intensity, and the third cylinder with a third intensity, respectively, wherein the first, the second and the third intensities are respectively corresponding to the intensities of the base portion, the recess and the engagement portion of the anchor expected in a topographic image for a material with which the base portion, the recess and the engagement portion of the anchor consist of.

14. The method of claim 13, wherein the determining step comprises the steps of
   (a.) matching the simulated image of the anchor onto the acquired topographic image of the anchor; and
   (b.) determining the orientation of the recess and the position of a top center of the base portion of the anchor from the position and orientation of the anchor determined from the simulated image of the anchor, so as to determining the orientation and the position of the anchor.

15. The method of claim 14, wherein the matching of the simulated image to the actual image of an anchor is performed with an optical flow registration algorithm.

16. A system for determining the position and orientation of an anchor attached to the skull of a patient from a topographic image of the anchor and the skull acquired therefrom, comprising a controller configured to perform the steps of:
   (a.) acquiring the topographic image of the anchor and the skull;
   (b.) defining a physical model of the anchor independently of the topographic image acquired;
   (c.) simulating an image of the anchor based on the physical model;
   (d.) matching the simulated image of the anchor onto the acquired topographic image
   (e.) determining the position and orientation of the anchor in the simulated image of the anchor; and
   (f.) determining the position and orientation of the anchor in the acquired topographic image based on the matching and the determined position and orientation of the anchor in the simulated image of the anchor.

17. The system of claim 16, further comprising means for acquiring the topographic image.

18. A method for positioning a platform of an image-guidance system in relation to the skull of a patient, comprising the steps of:
   (a.) attaching a plurality of anchors, $\{a_i\}$, i=1, ..., N, N being an integer greater than one, to the skull of a patient;
   (b.) acquiring a topographic image for each of the plurality of anchors $\{a_i\}$;
   (c.) simulating an image of the anchor $a_i$ that matches the acquired topographic image of the anchor $a_i$;
   (d.) determining the position and orientation of the anchor $a_i$ from the simulated image of the anchor $a_i$;
   (e.) determining the position and orientation of the anchor $a_i$ in the acquired topographic image of the anchor $a_i$ from the position and orientation of the anchor $a_i$ determined from the simulated image of the anchor $a_i$;
   (f.) repeating steps (b)-(e) for each and every one of the plurality of anchors, $\{a_i\}$, i=1, ..., N to obtain the position and orientation for each and every one of the plurality of anchors $\{a_i\}$ in the acquired topographic image; and
   (g.) using the obtained position and orientation for each and every one of the plurality of anchors $\{a_i\}$ to attach and align a corresponding platform to the plurality of anchors $\{a_i\}$;
wherein the simulating step comprises a step of modeling the anchor $a_i$ with a corresponding object that has a geometric shape simpler than that of the anchor $a_i$.

19. The method of claim 18, wherein the determining step comprises the step of matching the simulated image of the anchor to the acquired topographic image of the anchor.

20. A system for positioning a platform of an image-guidance system in relation to the skull of a patient, comprising a controller configured to perform the steps of:
   (a.) attaching a plurality of anchors, $\{a_i\}$, i=1, ..., N, N being an integer greater than one, to the skull of a patient;
   (b.) acquiring a topographic image for each of the plurality of anchors $\{a_i\}$;
   (c.) simulating an image of the anchor $a_i$ that matches the acquired topographic image of the anchor au
   (d.) determining the position and orientation of the anchor $a_i$ from the simulated image of the anchor au
   (e.) determining the position and orientation of the anchor $a_i$ in the acquired topographic image of the anchor $a_i$ from the position and orientation of the anchor $a_i$ determined from the simulated image of the anchor au
   (f.) repeating steps (b)-(e) for each and every one of the plurality of anchors, $\{a_i\}$, i=1, ..., N to obtain the position and orientation for each and every one of the plurality of anchors $\{a_i\}$ in the acquired topographic image; and
   (g.) using the obtained position and orientation for each and every one of the plurality of anchors $\{a_i\}$ to attach and align a corresponding platform to the plurality of anchors $\{a_i\}$;
wherein when the controller performs the simulating step, it performs a step of modeling the anchor $a_i$ with a corresponding object that has a geometric shape simpler than that of the anchor $a_i$.

* * * * *